United States Patent [19]

DeLuca

[11] Patent Number: 5,658,724
[45] Date of Patent: Aug. 19, 1997

[54] HERPES SIMPLEX VIRUS STRAINS DEFICIENT FOR THE ESSENTIAL IMMEDIATE EARLY GENES ICP4 AND ICP27 AND METHODS FOR THEIR PRODUCTION, GROWTH AND USE

[75] Inventor: Neal A. DeLuca, Cheswick, Pa.

[73] Assignee: University of Pittsburgh of the Commonwealth System of Higher Education, Pittsburgh, Pa.

[21] Appl. No.: 342,795

[22] Filed: Nov. 21, 1994

Related U.S. Application Data

[63] Continuation of Ser. No. 922,839, Jul. 31, 1992, abandoned.
[51] Int. Cl.$^6$ .............................. C12Q 1/70; C12N 7/04; C12N 5/10; C12N 15/86
[52] U.S. Cl. .................. 435/5; 435/172.3; 435/235.1; 435/325; 435/320.1; 435/236; 435/364
[58] Field of Search .......................... 435/69.1, 172.1, 435/172.3, 240.2, 320.1, 5, 235.1

[56] References Cited

U.S. PATENT DOCUMENTS

| | | | |
|---|---|---|---|
| 5,026,635 | 6/1991 | Ferguson et al. | 435/5 |
| 5,070,010 | 12/1991 | Hsu | 435/6 |
| 5,124,263 | 6/1992 | Temin et al. | 435/240.2 |

OTHER PUBLICATIONS

Johnson et al., "Improved Cell Survival by the Reduction of Immediate–Early Gene Expression in Replication–Defective Mutants of Herpes Simplex Virus Type 1 but Not by Mutation of the Virus Host Shutoff Function", J. Virol., Oct. 1994, pp. 6347–6362.

Werstuck et al., J. Of Virol., Mar. 1990, pp. 984–991, vol. 64, No. 3.

Kmetz et al., Nucleic Acid Res., vol. 16, No. 10, 1988, p. 4735.

Shih et al., PNAS, vol. 81, Sep. 1984, pp. 5867–5870.

Brakefield, X.O. and DeLuca, N.A., 1991, Herpes Simplex as a Vector for Neurons, in: Treatment of Genetic Diseases, Ed: Desnick, R.J., pp. 287–319; Churchill Livingston.

Chiocca, E. A., et. al., 1990, Transfer and Expression of the LacZ gene in Rat Brain Neurons Mediated by Herpes Simplex Virus Mutants. The new Biologist 2(8):739–746.

Breakfield, X.O. and DeLuca, N.A., 1991, Herpes Simplex Virus for Gene Delivery to Neurons, The New Biologist 3(3): 203–218.

DeLuca, N. A., et al., 1985, Isolation and Characterization of Deletion Mutants of HSV–1 in the Gene Encoding Immediate–Early Regulatory Protein ICP24. J. Virol. 56:558–570.

DeLuca, N.A. and Schaffer, P.A., 1987, Activities of Herpes Simplex Virus type 1 (HSV–1) ICP24 Genes Specifying Nonsense Peptides. Nucleic Acids Res. 15(11):4491–4511.

DeLuca, N.A. and Schaffer, P.A., 1988, Physical and Functional Domains of the Herpes Simplex Virus Transcriptional Regulatory Protein ICP4. J. Virol. 62:732–743.

Imbalzano, A.N., et al., 1991, Herpes Simplex Virus Transactivator ICP4 Operationally Substitues for the Cellular Transcription Factor SP1 for Efficient Expression of the Viral Thymidine Kinase Genes. J. Virol. 65:565–574.

McCarthy, A.M., et al., 1989, Herpes Simplex Virus Type 1 ICP27 Deletion Mutants Exhibit Altered Patterns of Transcription and are DNA Deficient. J. Virol. 63:18–27.

Paterson, T. and Everett, R.D., 1988, Mutational Dissection of the HSV–1 Immediate–early Protein Vmw175 Involved in Transcriptional Transactivation and Repression. Virology 166:186–186.

Paterson, T. and Everett, R.D., 1988, The Regions of the Herpex Simplex Virus Type 1 Immediate–Early Protein Vmw175 Required for Site Specific DNA Binding Closely Correspond to Those Involved in Transcriptional Regulation. Nucleic Acids Res. 16(23):11005–11025.

Shepard,A.A. et al., 1989, Separation of Primary Structural Components Conferring Autoregulation, Transactivation, and DNA–Binding Properties to the Herpes Simplex Virus Transcriptional Regulatory Protein ICP4. J. Virol. 63:3714–3728.

Shepard,A.A., et al., 1991, A Second–Site Revertant of a Defective Herpes Simplex Virus ICP4 Protein with Restored Regulatory Activities and Impaired DNA–Binding Properties. J. Virol. 65:787–795.

*Primary Examiner*—David Guzo
*Attorney, Agent, or Firm*—Leydig, Voit & Mayer, Ltd.

[57] ABSTRACT

Novel cell lines that express complementing levels of herpes simplex virus (HSV) essential immediate early proteins ICP4 and ICP27 and a method of producing the novel cell lines. These novel cell lines are utilized to provide novel HSV strains deficient for both ICP4 and ICP27, and their generation, and novel HSV strains deficient for ICP4 and ICP27 and one or more additional genes, and their generation. Vectors are provided from these methods of using these vectors for gene transfer and for producing site-specific homologous recombinations with cellular DNA.

60 Claims, 4 Drawing Sheets

HERPES SIMPLEX VIRUS STRAINS DEFICIENT FOR THE ESSENTIAL IMMEDIATE EARLY GENES ICP4 AND ICP27 AND METHODS FOR THEIR PRODUCTION, GROWTH AND USE

This is a continuation of application Ser. No. 07/922,839, filed Jul. 31, 1992, abandoned.

BACKGROUND OF THE INVENTION

The invention described herein was made in the course of work supported in part by Public Health Service Grant No. AI27431 from the National Institutes of Health, National Institute of Allergies and Infectious Diseases.

FIELD OF THE INVENTION

This invention relates to cell lines that express complementing levels of the herpes simplex virus essential immediate early proteins ICP4 and ICP27, and their generation and use; herpes simplex virus strains deficient for both ICP4 and ICP27, their generation, and use as vectors in various applications including, but not limited to, human gene therapy; herpes simplex virus strains deficient for ICP4 and ICP27 and one or more additional genes, and their generation and use as vectors in various applications including, but not limited to, human gene therapy; novel vectors comprising ICP4$^-$ICP27$^-$ HSV strains whose genome contains at least one exogenous gene and an appropriate promoter, and novel vectors comprising ICP4$^-$ICP27$^-$ additional HSV gene(s)$^-$ HSV strains whose genome contains at least one exogenous gene and an appropriate promoter; methods of using the novel HSV strains disclosed herein as vectors; and methods of using the hereinabove cited novel recombinant herpes simplex virus strains to direct homologous recombination with cellular DNA.

BACKGROUND OF THE INVENTION

Herpes simplex virus (HSV) contains a double-stranded, linear DNA genome comprised of approximately 152 kbp of nucleotide sequence, which encodes 75 genes. The viral genes are transcribed by cellular RNA polymerase II and are temporally regulated, resulting in the transcription and subsequent synthesis of gene products in roughly three discernable phases. These phases, or kinetic classes of genes are referred to as the Immediate Early (IE, or $\alpha$), Early (E, or $\beta$) and Late (L, or $\gamma$) genes. Immediately following the arrival of the genome of a virus in the nucleus of a newly infected cell, the IE genes are transcribed. The efficient expression of these genes does not require prior viral protein synthesis. The products of IE genes are required to activate transcription and regulate the remainder of the viral genome.

One IE protein, Infected Cell Polypeptide 4 (ICP4), also known as $\alpha$4, or Vmw175, is absolutely required for both virus infectivity and the transition from IE to later transcription. Owing to its complex, multifunctional nature and its central role in the regulation of HSV gene expression, ICP4 has been the subject of numerous genetic and biochemical studies. (See DeLuca, N. A. et al., *Nucleic Acids Res.*, 15:4491–4511, 1987; DeLuca, N. A. et al., *J. Virol.*, 62:732–743, 1988; Paterson, T. et al., *Virology*, 166:186–196, 1988; Paterson, T. et al., *Nucleic Acids Res.*, 16:11005–11025, 1988; Shepard, A. A. et al., *J. Virol.*, 63:3714–3728, 1989; and Shepard, A. et al., *J. Virol.*, 65:787–795, 1991.) Aiding in these studies was the development of a system to grow herpes viruses that contain mutations which inactivate essential viral proteins. In this case, cell lines were generated by cotransformation with a plasmid DNA that encoded the neomycin resistance gene from *E. coli* under the control of SV 40 early promoter and a plasmid encoding the wild-type ICP4 gene. (See DeLuca, N. A. et al., *J. Virol.*, 56:558–570, 1985 and DeLuca, N. A. et al., *Nucleic Acids Res.*, 15:4491–4511, 198.) These stable cell lines were used to generate and propagate mutant viruses that are void of ICP4 activity. (See DeLuca, N. A. et al., *J. Virol.*, 56:558–570, 1985; DeLuca, N. A. et al., *J. Virol.*, 62:732–743, 1988; Imbalzano, A. et al., *J. Virol.*, 65:565–574, 1991; Shepard, A. A. et al., *J. Virol.*, 63:3714–3728, 1989; and Shepard, A. et al., *J. Virol.*, 65:787–795, 1991.) Since the first report of this approach to HSV genetics, numerous studies have followed utilizing this strategy.

From the phenotype of viruses deleted in ICP4, it became evident that such viruses would be potentially useful for gene transfer purposes. Several studies have been published exploring the potential use of such viruses for gene transfer. (See Breakefield, X. O. et al., *Treatment of Genetic Diseases*, (Churchill Livingstone, Inc.), 1991 and Chocca, E. A. et al., *The New Biologist*, 2:739–746, 1990.) One property of viruses deleted for ICP4 that makes them desirable for gene transfer is that they only express the four other IE genes ICP0, ICP27, ICP22 and ICP47. (See DeLuca, N. A. et al., *J. Virol.*, 56:558–570, 1985.) This excludes the expression of viral genes encoding proteins that direct viral DNA synthesis, as well as the structural proteins of the virus. This is desirable from the standpoint of minimizing possible deleterious effects on host cell metabolism following gene transfer.

Despite the fact viruses deleted for ICP4 are blocked at the earliest stage of infection genetically possible subsequent to the delivery of the genome to the host cell nucleus, two phenomena have complicated the use of such viruses for effective gene transfer, or therapy. First, viruses deleted for essential genes, such as ICP4-deficient viruses, require that they are propogated on culture cells engineered to contain and express the gene deleted from the virus. (See DeLuca, N. A. et al., *J. Virol.*, 56:558–570, 1985.) This often results in a sub-population of viruses that are no longer deleted for that gene due to homologous recombination events between the mutant viral genome and the wild-type gene resident in the host cell genome. (See DeLuca, N. A. et al., *J. Virol.*, 56:558–570, 1985.) In some cases, this is minimized by deleting from the virus HSV sequences flanking the deleted gene and excluding these sequences from the plasmid used to generate the permissive transformed cell line. Therefore, the gene resident in the transformed cell line does not have flanking nucleotide sequence homology on both sides to promote homologous recombination. This is the case for the ICP4 deletion virus-transformed cell line pair, d120—E5 cells (See DeLuca, N. A. et al., *J. Virol.*, 56:558–570, 1985 and DeLuca, N. A. et al., *Nucleic Acids Res.*, 15:4491–4511, 1987) and the ICP27 deletion virus-transformed cell line pair, 5dl 1.2–2–3 cells. (See McCarthy, A. M. et al., *Virol.*, 63:18–27, 1989).

Secondly, despite only expressing the four other immediate early proteins, ICP4-deficient viruses are toxic to cells in culture and presumably to the majority of cells in an animal. This is most probably due to the expression of one or more of the remaining immediate early proteins and not primarily due to components of the incoming capsid since certain defective HSV virus particles, which contain all the capsid components and none of the IE genes, are not toxic. Despite attempts to alleviate these problems, a need exists for defective herpes simplex virus strains that exhibit efficient growth in a controlled laboratory complementing system, a lower level of wild-type virus regeneration and lowered cytotoxic effects.

SUMMARY OF THE INVENTION

The present invention provides for novel cell lines which contain DNA encoding for the HSV proteins ICP27 and ICP4. The present invention also provides for a method of producing the novel ICP4$^+$ICP27$^+$ cell lines. The method comprises cotransfecting a piece of DNA encoding for ICP27 and a piece of DNA encoding for ICP4 into a suitable cell line and selecting cells which simultaneously harbor both ICP4 and ICP27 encoding DNA. Suitable cell lines include any cell line which will host HSV and which will form colonies. The pieces of DNA encoding ICP27 or ICP4 may be introduced into the cell using any DNA delivery system, such as, for example, retroviral vectors, liposome technology, and recombinant plasmids.

The present invention provides for a method of using the novel ICP4$^+$ICP27$^+$ cell lines to produce recombinant HSV strains deficient for both ICP4 and ICP27. The method comprises coinfecting ICP4$^+$ICP27$^+$ cells with viruses deficient in ICP4 and viruses deficient in ICP27 and assaying for recombinant ICP4$^-$ICP27$^-$ progeny virus.

The present invention provides for the novel recombinant ICP4$^-$ICP27$^-$ HSV strains discussed hereinabove. The present invention also provides a method of efficiently growing the recombinant ICP4$^-$ICP27$^-$ HSV strains with an extremely low level of wild-type regeneration. The method comprises infecting ICP4$^+$ICP27$^+$ cells with a recombinant ICP4$^-$ICP27$^-$ HSV strain and collecting the progeny virus. The inventor has obtained stock titers in excess of $10^9$ plaque forming units (PFU) per milliliter (ml). The frequency of appearance of wild-type recombinant virus in the transformed cell line is calculated at $10^{-12}$. This represents an extremely low ratio of wild-type recombinants to infectious units (PFU). The present invention also provides for novel vectors comprising ICP4$^-$ICP27$^-$ HSV strains whose genome contains at least one exogenous gene to be transferred to a cell under the control of the appropriate promoter sequence for purposes including, but not limited to, human gene therapy or the generation of novel cell lines.

The present invention provides for the novel recombinant ICP4$^-$ICP27$^-$ additional HSV gene(s)$^-$ HSV strains. Some of these recombinant ICP4$^-$ICP27$^-$ additional HSV gene(s)$^-$ HSV strains will be transcriptionally silent. Many of the genes within the HSV genome are nonessential to virus reproduction in the ICP4ICP27 complementing cell lines. Nonessential genes are those which are nonessential for growth on ICP4ICP27 complementing cell line. The present invention provides for ICP4$^-$ICP27$^-$ additional HSV gene(s)$^-$ HSV strains which are ICP4$^-$ICP27$^-$ nonessential HSV gene(s)$^-$ HSV strains.

By using the novel ICP4$^+$ICP27$^+$ cell lines and the novel recombinant ICP4$^-$ICP27$^-$ HSV strains, the present invention provides methods of producing novel recombinant HSV strains deficient for both ICP4 and ICP27 and also deficient for one or more additional HSV genes, such as, for example, ICP0.

The present invention provides for methods of efficiently growing the recombinant ICP4$^-$ICP27$^-$ nonessential HSV gene(s)$^-$ HSV strains with an extremely low level of wild-type regeneration. These methods are identical with the methods cited hereinabove for efficiently growing novel recombinant ICP4$^-$ICP27$^-$ HSV strains since no proteins encoded by IE genes besides ICP4 and ICP27 are needed for virus replication. The invention provides for novel vectors comprising ICP4$^-$ICP27$^-$ HSV strains whose genome contains at least one exogenous gene to be transferred to a cell under the control of an appropriate promoter sequence. The present invention also provides for novel vectors comprising ICP4$^-$ICP27$^-$ additional HSV gene(s)$^-$ HSV strains whose genome contains at least one exogenous gene to be transferred to a cell under the control of an appropriate promoter sequence.

Finally, the present invention provides for a method of using the hereinabove cited novel HSV strains to direct homologous recombination between cellular sequences cloned into the HSV genome and cellular DNA. The method comprises infecting cells with large amounts of a novel vector, wherein the vector comprises an ICP4$^-$ICP27$^-$ HSV strain whose genome contains a gene homologous to a gene existing within the cells or wherein the vector comprises an ICP4$^-$ICP27$^-$ additional HSV gene(s)$^-$ HSV strain whose genome contains a gene homologous to a gene existing within the cells.

It is an object of the present invention to provide novel cell lines which contain DNA encoding for the HSV proteins ICP27 and ICP4.

It is a further object of the present invention to provide a method for producing ICP4$^+$ICP27$^+$ cell lines.

It is a further object of the present invention to provide a method of using ICP4$^+$ICP27$^+$ cell lines to produce HSV strains deficient for the genes encoding the HSV proteins ICP4 and ICP27.

It is a further object of the present invention to provide novel ICP4$^-$ICP27$^-$ HSV strains.

It is a further object of the present invention to provide a method of growing ICP4$^-$ICP27$^-$ HSV strains using ICP4$^+$ICP27$^+$ cell lines.

It is a further object of the present invention to provide ICP4$^-$ICP27$^-$ additional HSV gene(s)$^-$ HSV strains.

It is a further object of the present invention to provide a method of producing ICP4$^-$ICP27$^-$ additional HSV gene(s)$^-$ HSV strains using ICP4$^+$ICP27$^+$ cell lines.

It is a further object of the present invention to provide a method of growing ICP4$^-$ICP27$^-$ additional HSV gene(s)$^-$ HSV strains using ICP4$^+$ICP27$^+$ cell lines.

It is a further object of the present invention to provide novel vectors comprising ICP4$^-$ICP27$^-$ HSV strains whose genome contains at least one exogenous gene to be transferred to a cell under the control of an appropriate promoter sequence.

It is a further object of the present invention to provide novel vectors comprising ICP4$^-$ICP27$^-$ additional HSV gene(s)$^-$ HSV strains whose genome contains at least one exogenous gene to be transferred to a cell under the control of an appropriate promoter sequence.

It is a further object of the present invention to provide a method of using the novel HSV strains disclosed as vectors.

It is a further object of the present invention to provide a method of using the disclosed novel HSV strains to direct homologous recombination between cellular sequences cloned into the HSV genome and cellular DNA.

These and other objects of the invention will be more fully understood from the following description of the invention with reference to the figures incorporated herein as a part to this application.

DESCRIPTION OF THE PREFERRED EMBODIMENTS

As used herein, "herpes simplex virus" (HSV) means both type 1 HSV and type 2 HSV.

As used herein, "ICP4$^-$ICP27$^-$ HSV strain" means an HSV strain deficient for the HSV genes encoding ICP4 and ICP27.

As used herein, "ICP4$^-$ICP27$^-$ additional HSV gene(s)$^-$ HSV strain" means an HSV strain deficient for the HSV genes encoding ICP4, ICP27, and one or more additional HSV genes.

As used herein, "nonessential HSV gene" means an HSV gene which is nonessential to HSV replication in an ICP4ICP27 complementing cell line.

As used herein, "ICP4$^-$ICP27$^-$ nonessential HSV gene (s)$^-$ HSV strain" means an HSV strain deficient for the HSV genes encoding ICP4, ICP27, and one or more nonessential HSV genes.

As used herein, "ICP4$^-$ICP27$^-$ additional IE gene(s)$^-$ HSV strain" means an HSV strain deficient for the genes encoding ICP4, ICP27, and one or more additional immediate early HSV genes.

As used herein, "nonessential region" means a region of a genome of an HSV strain where an exogenous gene may be inserted without interfering with virus function.

The present invention provides for novel cell lines containing DNA encoding for both the HSV proteins ICP27 and ICP4. The present invention also provides a method of producing a cell line containing DNA encoding for both the HSV proteins, ICP4 and ICP27, wherein the method comprises cotransfecting cells capable of hosting HSV with pieces of DNA encoding the HSV protein ICP4, and pieces of DNA encoding the HSV protein ICP27; incubating said cells; and selecting cells harboring both ICP4 and ICP27 encoding pieces of DNA.

The pieces of DNA encoding ICP27 or ICP4 may be introduced into the cell using any DNA delivery system, such as, for example, retroviral vectors, recombinant plasmids, and liposome technology. Cells harboring both ICP4 and ICP27 encoding pieces of DNA may be selected by any available method. For example, the present invention encompasses the method of cotransfecting cells capable of hosting HSV with a piece of DNA encoding the HSV protein ICP4, a piece of DNA encoding the HSV protein ICP27, and a piece of DNA encoding a selection factor; incubating the cells; and selecting cells expressing DNA encoding for the selection factor. A selection factor can be anything which will allow for the selection of a cell, such as, for example, a neomycin resistance protein.

A novel ICP4ICP27 complementing cell line was produced as follows: Plasmids encoding the genes for ICP27 and ICP4 (shown in FIG. 1) were cotransfected with the plasmid pSV2neo into Vero cells and selected with the antibiotic G418. G418 resistant colonies were amplified and tested for the ability to host KOS (wild-type virus), an ICP4$^-$ virus, d120, and an ICP27$^-$ virus, 5dl 1.2. All possibilities were obtained: cells that host KOS (all cell lines were able to host KOS), cells that host only d120, cells that host 5dl 1.2, and cells that host both d120 or 5dl 1.2. Curiously, cells that hosted only the ICP27$^-$ virus were far fewer in number than all the other types of cells obtained. Of interest were the cell lines that hosted both d120 and 5dl 1.2. One cell line, designated 26 cells, yielded 900 PFU per cell d120 and 350 PFU per cell 5dl 1.2. Another cell line, designated 8 cells, was retained because it was the only cell line that efficiently hosted 5dl 1.2 and not d120.

Although Vero cells were used in the procedure described hereinabove, it will be appreciated that the present invention encompasses use of any cell line which will host HSV and which will form colonies.

It will be further appreciated that the present invention encompasses use of any delivery system for the pieces of DNA encoding the HSV proteins ICP4 or ICP27 and which will transfect the cell lines utilized. It is preferred that the DNA fragments used to incorporate the ICP4 and ICP27 genes into the cell lines have as few as possible non-coding base pairs on their 3' and 5' ends to limit the generation of wild-type recombinant virus.

Although the plasmid pSV2neo and the antibiotic G418 were used in the procedure described hereinabove, it will be appreciated that the present invention encompasses use of any piece of DNA encoding a selection factor and any accompanying compound or technique that allows for selection of cells hosting the selection factor. It will further be appreciated that the present invention encompasses transfecting only ICP4 and ICP27 encoding pieces of DNA and using any system which allows for selection of cells harboring the ICP4 and ICP27 encoding DNA pieces. It will further be appreciated that the present invention encompases the use of any means of introducing ICP4$^+$, ICP27$^+$ and selection factor genes into cells including but not limited to retroviral vectors, recombinant plasmids, and liposomes.

Although HSV-1 KOS wild-type virus was used in the procedure described hereinabove, it will be appreciated that the present invention encompasses use of any wild-type HSV-1 or HSV-2 virus containing both the ICP4 and ICP27 genes.

Although d120 and 5dl 1.2 were used in the procedure described hereinabove, it will be appreciated that the present invention encompasses use of any ICP4$^-$ or ICP27$^-$ HSV strains.

The method of producing a novel ICP4$^+$ICP27$^+$ cell line disclosed hereinabove is unique in that those skilled in the art would not have thought it possible to get a significant number of cells accepting both the cotransfected pieces of DNA encoding for ICP4 and pieces of DNA encoding for ICP27 and have those cells express complementing levels of both ICP4 and ICP27. The prior art teaches that such a method would produce almost solely ICP4$^+$ or ICP27$^+$ or ICP4$^-$ICP27$^-$ cell lines. Furthermore, the prior art teaches that the toxic effects of the two ICP4$^+$ and ICP27$^+$ vectors may kill any ICP4$^+$ICP27$^+$ cells almost immediately. Despite the need for such cell lines, prior research has taught that such a method would not be efficient enough to produce a cell line hosting both ICP4$^+$ and ICP27$^+$ vectors.

Production of the novel ICP4⁺ICP27⁺ cell lines has allowed the inventor to provide for novel recombinant HSV strains deficient for both ICP4 and ICP27. The present invention provides a method of producing an HSV strain whose genome is deficient for the HSV genes encoding for ICP4 and ICP27, wherein the method comprises coinfecting ICP4ICP27 complementing cells containing DNA encoding for the HSV proteins ICP4 and ICP27 with an HSV strain deleted for the ICP4 gene and an HSV strain deleted for the ICP27 gene; incubating the cells; plating virus progeny from the incubuted bated cells on the ICP4ICP27 complementing cells, ICP27 complementing cells, ICP4 complementing cells; and ICP4⁻ICP27⁻ cells; picking plaques; and identifying virus that plaque on ICP4ICP27 complementing cells and do not plaque on ICP27 complementing cells, ICP4 complementing cells, or ICP4⁻ICP27⁻ cells.

Novel ICP4⁻ICP27⁻ HSV strains were produced as follows: 26 cells were coinfected with d120 and 5dl 1.2, plating the progeny on 26 cells, picking plaques, and identifying isolates that plaque on 26 cells and do not plaque on 8 cells (ICP27 complementing), E5 cells (ICP4 complementing), or Vero cells. These corresponded to 8% of the total progeny; a frequency consistent with the distance between ICP4 and ICP27. Individual plaque isolates that only grew on 26 cells were examined by Southern blot hybridization to ascertain the presence of both mutations in cis. One such isolate (d92) was chosen for further study.

A Southern blot was conducted to compare regions of the genome encoding ICP4 and ICP27 from KOS, d120, 5dl 1.2 and d92. The probe for ICP27 was the fragment used to generate the 26 cell line. It hybridizes to the indicated Nru I fragment in wild-type virus and in d120, and to a deleted form of the Nru I fragment in 5dl 1.2 and d92. The probe used for ICP4 was also the same used to generate the 26 cell line, except that the ICP4 promoter was not present in the probe. It hybridized to the indicated ICP4 containing fragments, Bam HI K, P, Y and M'. M' runs off the gel because of its small size. d120 and d92 show the characteristic deletion pattern consistent with the documented 4.1 kb deletion. The heterogeneity in the size joint Bam HI fragment is due to variation in the number of "a" sequences in individual genomes. Therefore, d92 contains the intended deletions in ICP4 and ICP27, and behaves functionally as a double deletion mutant.

Although Veto cells were used in the procedure described hereinabove, it will be appreciated that the present invention encompasses use of any cell line which will host HSV and which will form colonies.

Although E5 cells and 8 cells were used in the procedure described hereinabove, it will be appreciated that the present invention encompasses the use of any ICP4 complementing cells and any ICP27 complementing cells.

Although d120 and 5dl 1.2 were used in the procedure described hereinabove, it will be appreciated that the present invention encompasses use of any ICP4⁻ or ICP27⁻ HSV strains.

Figure 1:
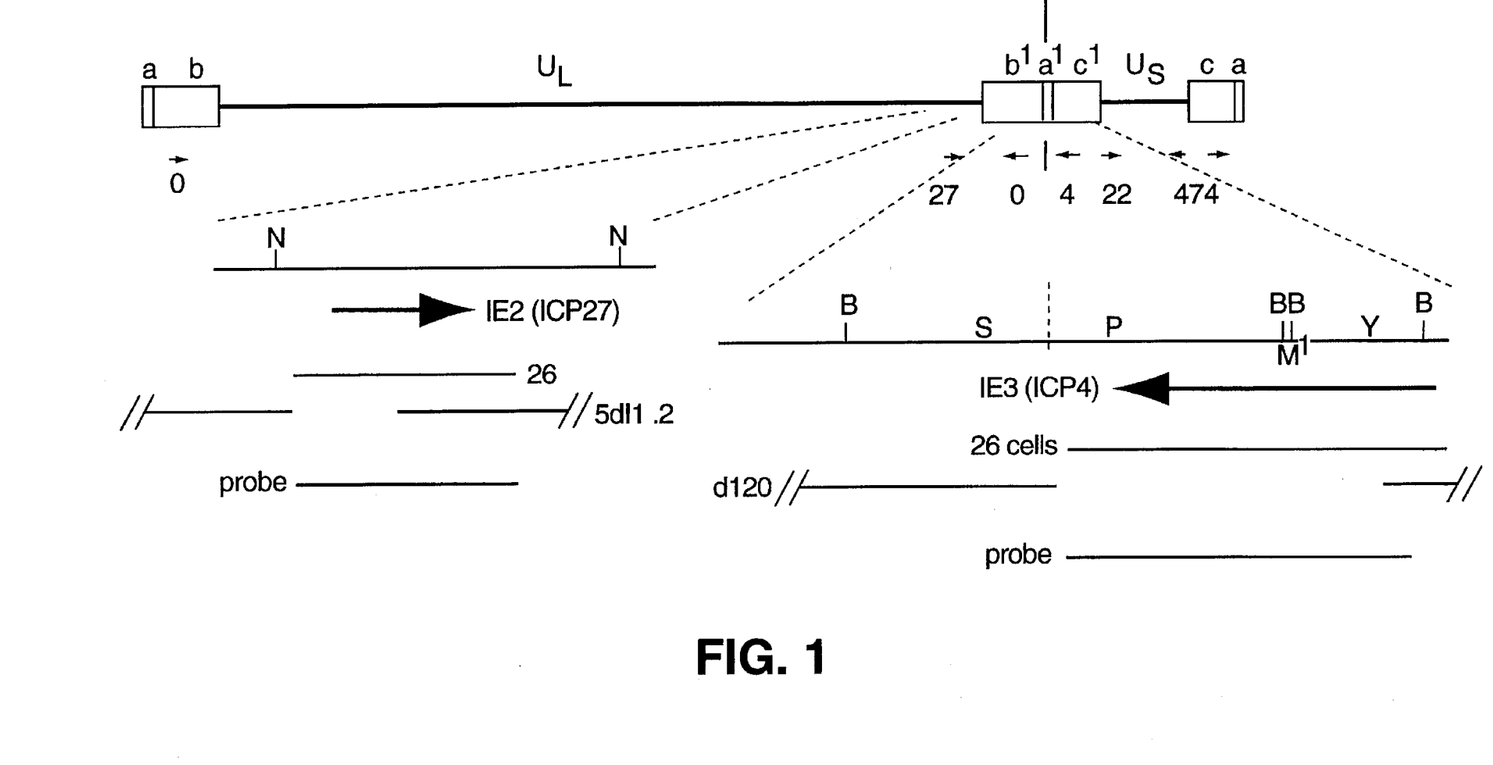
FIG. 1 shows representations of the HSV genome, the genes encoding for ICP27 and ICP4, the 5dl 1.2 and d120 virus genomes with their ICP27 and ICP4 encoding fragments delineated, ICP27 and ICP4 probes.

It is preferred that the ICP4 or ICP27 deletions in the ICP4⁻ and ICP27⁻ viruses be as large as possible. As shown in FIG. 1, the deletions in these viruses extend beyond the sequence of the DNA fragments used to incorporate the ICP27 and ICP4 genes in the complementing cell line. Therefore, the copies of these genes resident in the transformed cell line lack the flanking homology necessary to rescue either of the mutations in the double mutant viral genome by homologous recombination.

The present invention provides for methods of efficiently growing the novel ICP4⁻ICP27⁻ HSV strains disclosed herein. The method comprises infecting 26 cells with the novel ICP4⁻ICP27⁻ HSV strains, incubating the infected cells, and collecting the progeny virus. Due to the efficiency of these cell lines, the inventor has been able to obtain stock titers of this virus in excess of $10^9$ plaque forming units (PFU) per milliliter. This demonstrates efficient growth in the complementing cells. The prior art teaches that such growth should not be produced. This efficiency ensures that additional genetic manipulations of the virus that have relatively mild growth damping effects may be performed, such as deletion of the remaining IE genes. The high titers obtainable in this system are also in great excess of those obtained with any of the currently used viral vector systems known to the inventor.

As far as viral vector systems are concerned the ICP4⁻/ICP27⁻ system described herein is considered a "helper-virus free" system. Most "helper-virus free" systems are notorious for the generation of wild-type, potentially pathogenic recombinants. Until now, the best one has been able to do with a herpes virus system is a frequency of wild-type generation somewhat less than $10^{-6}$. Due to its construction, the ICP4⁻/ICP27⁻ system described herein has a theoretical wild-type generation frequency less than $10^{-12}$.

The methods of producing and growing the novel recombinant ICP4⁻ICP27⁻ HSV strains is novel in that novel ICP4⁺ICP27⁺ cell lines are utilized.

Long continuous protein labelling pattern for uninfected (M), KOS-, d120, 5dl 1.2- and d92-infected cells were compared. All viruses show some degree of shut off of host cell protein synthesis. This is probably due to the virion associated shut off gene, vhs. The only discernable viral protein present in the d92 profile is ICP6, the large subunit of ribonucleotide reductase. The absence of ICP0 in this long term label is probably due to an alteration in the stability of ICP0 as a function of the absence of ICP27. ICP0 is made to the same degree in d92 as in d120 in pulse labelling experiments. ICP27 alters the phosphorylation of a variety of proteins, including ICP0. There data demonstrate that d92 does not express ICP27 or the 175 kd ICP4 protein.

In order to assess the utility of d92 and its potential derivatives as a gene transfer vector, experiments were performed to determine if and for how long d92 genomes can functionally persist in infected cells. The basis for the measurement is the ability to rescue d92 genomes via complementation with an infecting virus that has a mutation in an essential gene other than ICP4 or ICP27. This method is illustrated schematically in FIG. 2.

Figure 2:
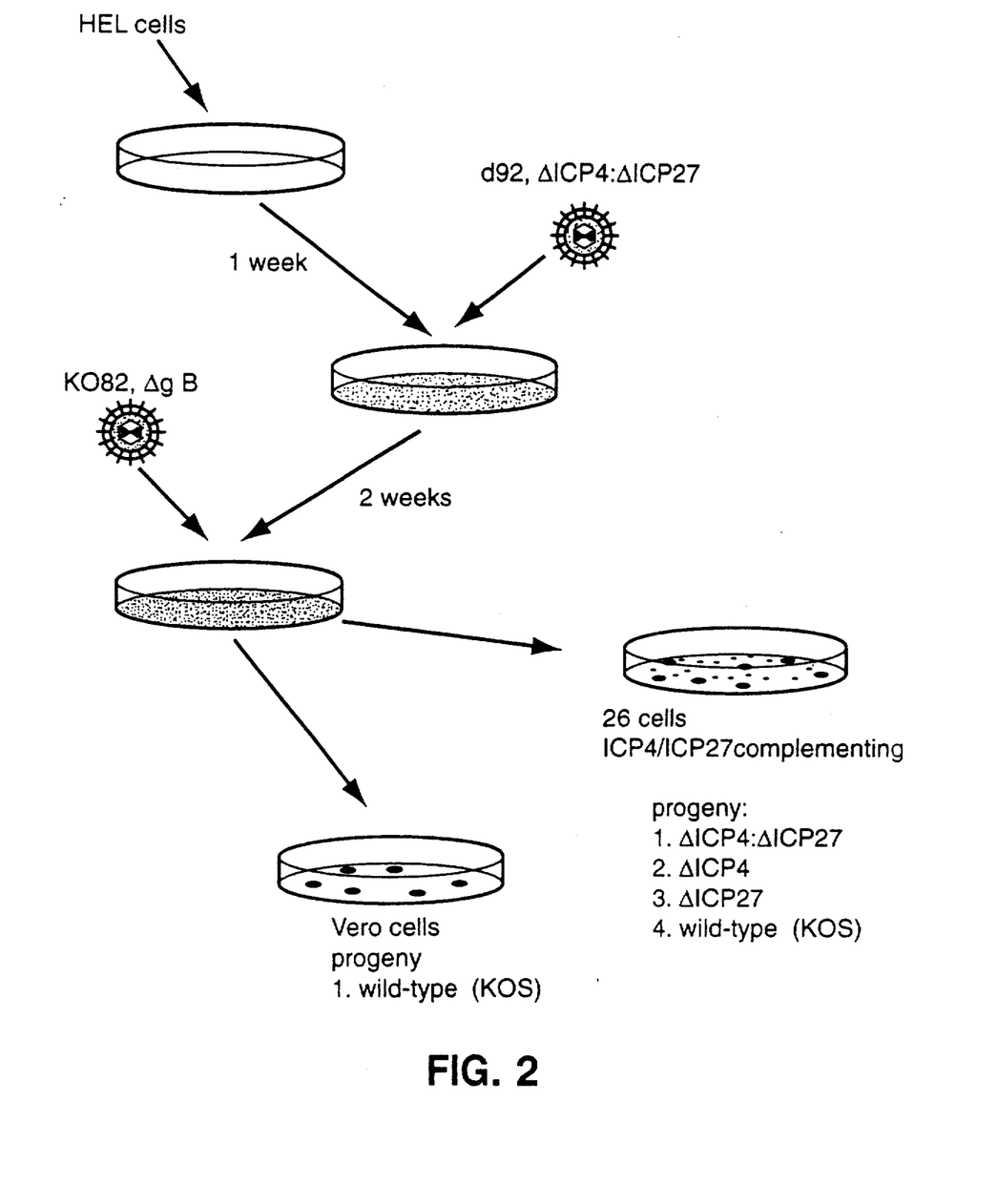
FIG. 2 shows the general method of producing d92-persistently infected HEL cells, the reactivation of virus with HSV K082 and the assay for reactivating virus on 26 cells and Vero cells.

As a direct indication of the usefulness of d92, and any of its derivatives, the following experimental approach was adopted (FIG. 2). One week old confluent normal human (primary) fibroblasts (HEL) cells were infected with d92 at a range of multiplicities of infection from 0.1 to 10 PFU/cell. At 3 and 10 PFU/cell cytopathic effects were seen at 48 hours post-infection that were less pronounced than with d120. All the infected monolayers of HEL cells were completely restored by one week post-infection. At two weeks post-infection, the monolayers were infected with K082 (moi =3PFU/cell), a gB deletion mutant that requires gB transformed cells for growth. 18 hours later, the monolayers were harvested for quantitation of infectious virus.

Figure 3:
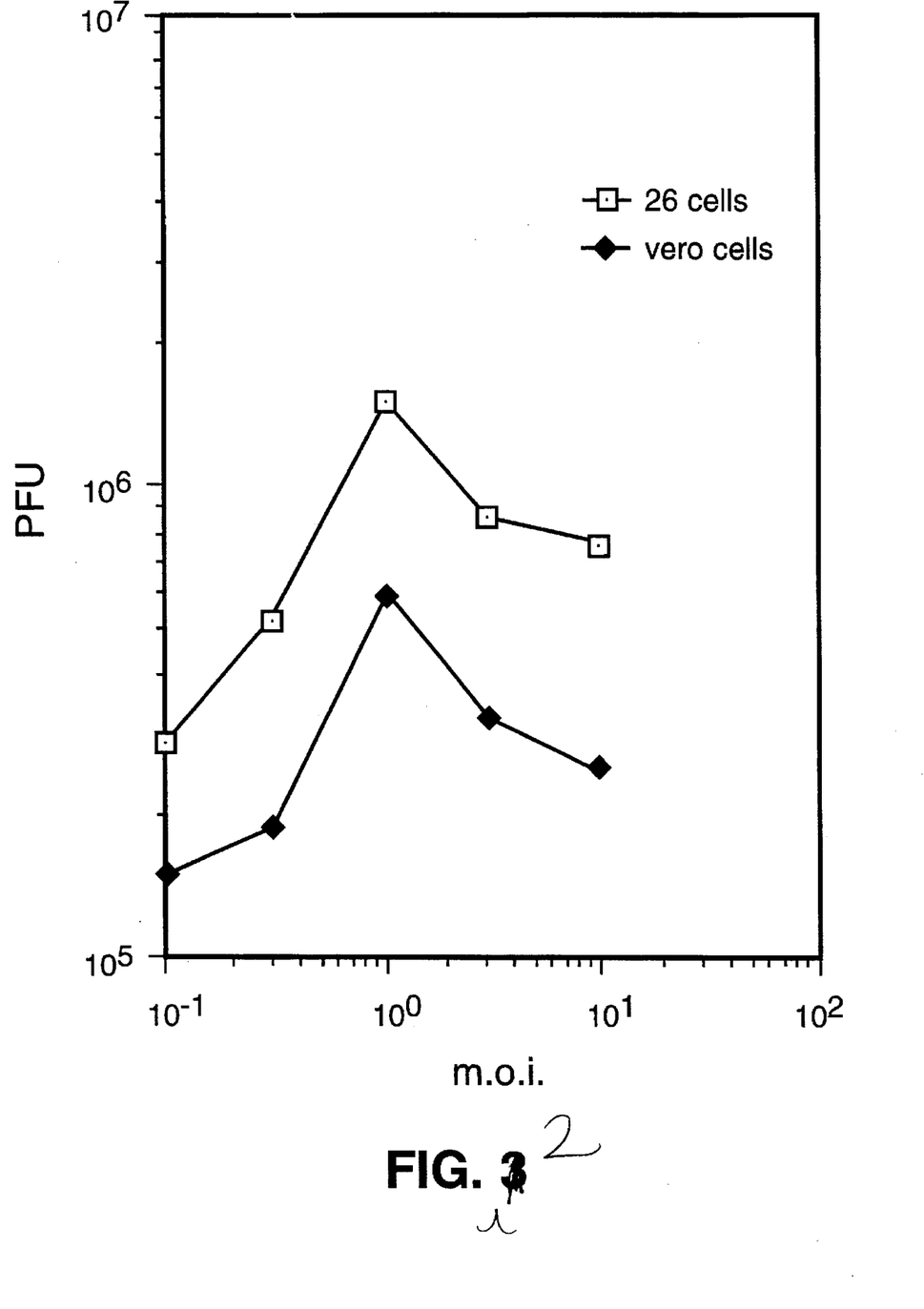
FIG. 3 is a graph of titers of progeny that can be reactivated from human embrionic lung cells persistently infected with d92, which plate on 26 cells and on Vero cells as a function of initial input of d92. 26 cells are an ICP4$^+$ ICP27$^+$ cell line.

Shown in FIG. 3 are the titers of progeny that plate on 26 cells and on Vero cells as a function of initial input of d92. Three important observations can be made from the data shown in FIG. 3: (1) Substantial amounts of virus could be obtained from the week old infected cultures at all the multiplicities tested. No virus was obtained from cells infected with d92 at any of the multiplicities if the cells were not infected with K082; (2) The yield of the progeny on 26 cells was three fold higher and the plaques were smaller than that on Vero cells. Southern blots on progeny picked off of 26 cells demonstrated the presence of the deletions in ICP4 and ICP27 in the rescued virus population; and (3) The yield of virus increased linearly up to 1 PFU/cell after which the yield decreased.

From these results it is clear that a substantial number of functional d92 genomes persisted in the infected HEL cells at two weeks post-infection. Moreover, the cells retained viability sufficient to support HSV infection. The appearance of progeny on Vero cells is due to recombination between the persistent d92 genomes and the infecting K082 genomes. This is to be expected given the genomic distance between gB and ICP27. The decline in virus yield for moi's of d92 greater than 1 most probably reflects the residual cytotoxicity of d92.

Figure 4:
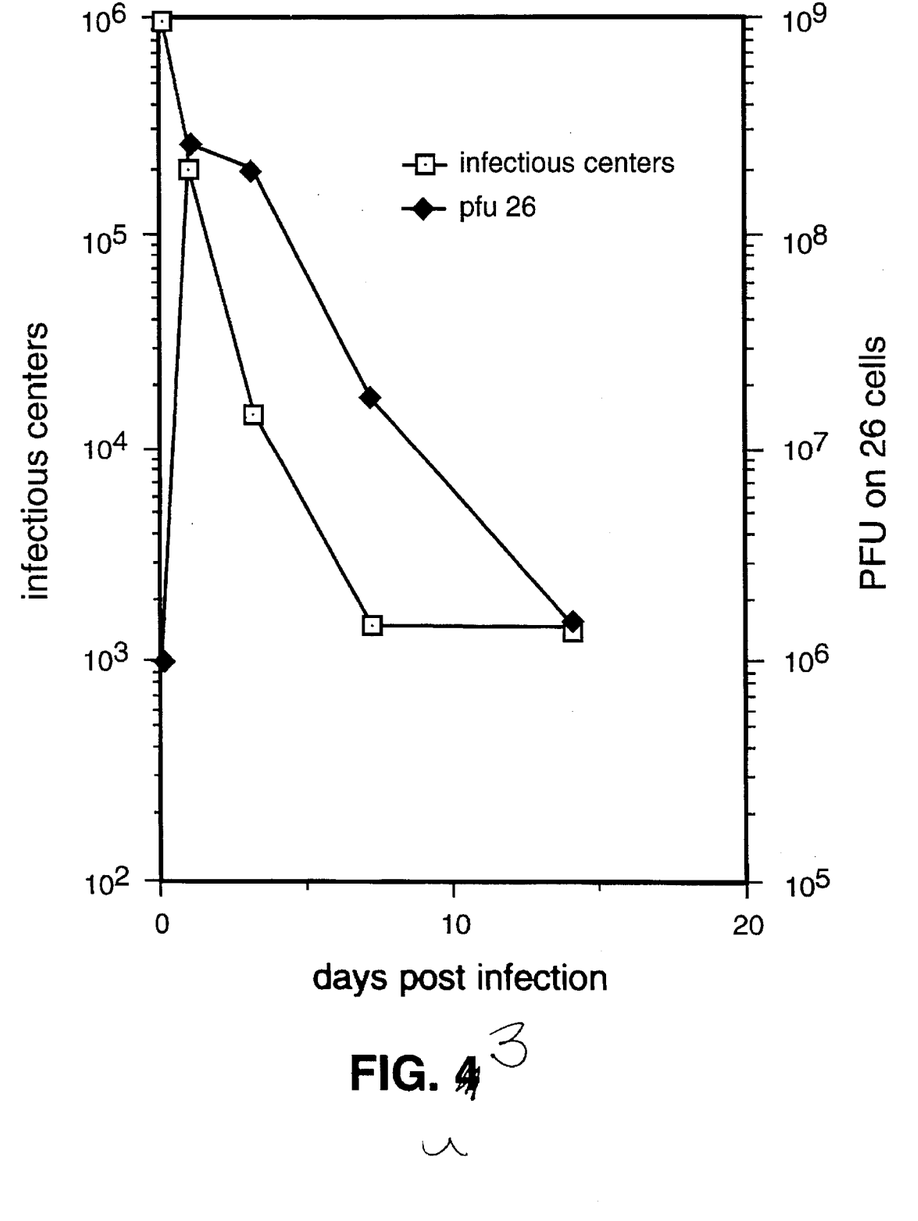
FIG. 4 is a graph of infectious centers and virus yield resulting from reactivation of d92-persistently infected HEL cells measured on 26 cells, as a function of time post-infection.

In the experiment discussed hereinabove it was established that the greatest number of functional d92 genomes persist in the HEL cells when an moi of 1 PFU/cell was used. The following experiment was performed in order to determine the number of functional persistent genomes as a function of time post-infection. Cultures of $10^6$ one week old HEL cells were infected with d92 at an moi of 1 PFU/cell. At 1, 3, 7 and 14 days post-infection the cultures were infected with K082 at an moi of 3 and incubated for 5 hours for infectious centers, or 18 hours for total virus yield. For infectious centers, the monolayers were trypsinized, diluted and plated on 26 and Vero cells. For total virus yield, the monolayers were scraped into the medium, freeze-thawed, and sonnified. The suspension was then clarified by centrifugation, diluted and plated on 26 and Vero cells. As before, the number of plaques on 26 cells was always about 2 to 4 times the number of Vero cells. Shown in FIG. 4 are the infectious centers and virus yield measured on 26 cells, as a function of time post-infection. The infectious center assay was problematic in that it was not possible to obtain single cell suspensions. If the infectious center assay were accurate, then the burst size of d92 at 3 and 7 days would be $10^4$. Wild-type HSV under optimum conditions is $10^3$.

From the burst experiment, an estimate that there are at least $10^4$ functional genomes (to give $2\times10^6$ rescued progeny) persisting at two weeks post-infection is obtained. It is not known whether there are more intact genomes in the cells that are not rescued, or whether parts of the 150 kb genome are also present in some cells.

Given that ICP27 and ICP4 are the only absolutely essential genes that are expressed during the IE phase of viral gene expression, and that functional IE genes are required for expression of the remainder of the vital genome, it follows that deletion of ICP's 4 and 27 allow for the deletion or inactivation of the remainder of the IE genes, generating a viral genome that is transcriptionally silent in the absence of exogenously added ICP4 or 27. The generation of a viral genome that will enter the nucleus and not express any of its encoded genes will eliminate the cytotoxic effects associated with the expression of IE proteins. This will allow for the expression of a foreign gene (under the appropriate promoter control) from the efficiently delivered HSV genome without cytotoxic side effects. This is desirable from the standpoint of safe and efficient gene therapy schemes.

So far, the production of a virus (d92) that is deficient for the only two essential IE genes, ICP4 and ICP27 has been described. The expression of viral genes in the d92 background is limited to ICP6, ICP0, ICP22 and ICP47. Although the ICP0 protein is expressed from the d92 genome, its stability may be reduced due to the absence of ICP27 gene product. As previously stated, an important feature of this system is that the flanking homologies necessary to rescue the deletions in the virus (d92) are not present with the genes resident in the complementing cell line (26 cells). Therefore, the generation of wild-type recombinants is an extremely improbable event, and in practice, they are not seen. This is extremely important not only from the standpoints of the development of "safe" vectors but also for the ability to delete other viral genes (such as for example ICP0) that may have a growth dampening effect.

The present invention provides for novel HSV strains deficient for ICP4, ICP27, and one or more additional HSV genes, including HSV strains deficient for all IE genes. Some of these HSV strains will be transcriptionally silent in the absence of exogenously added ICP4 and ICP27. The generation of a viral genome that will enter the nucleus and not express any of its encoded genes will eliminate the cytotoxic effects associated with the expression of IE proteins. This will allow for the expression of a foreign gene (under the appropriate promoter control) from the efficiently delivered HSV genome without cytotoxic side effects. This is desirable from the standpoint of safe and efficient gene therapy schemes.

The present invention provides methods of generating ICP4⁻ICP27⁻ nonessential HSV gene(s)⁻ HSV strains. One method comprises coinfection of the ICP4ICP27 complementing cell line with the ICP4⁻ICP27⁻ HSV strain and an HSV strain harboring a deletion in the desired nonessential gene. At some frequency homologous recombination will generate a ICP4⁻ICP27⁻ nonessential gene⁻ recombinant virus. The progeny of this coinfection is then plated on ICP4ICP27 complementing cells and ICP4⁻ICP27⁻ nonessential gene(s)⁻ HSV strains are selected. Since there is no genetic selection for the ICP4⁻ICP27⁻ nonessential gene⁻ virus, Southern blot analysis of individual progeny isolates may be utilized to select ICP4⁻ICP27⁻ nonessential gene(s)⁻ HSV strain. The method may be performed again to produce further nonessential gene deletions using the new ICP4⁻ICP27⁻ nonessential gene⁻ HSV strain and an HSV strain harboring a deletion in another desired nonessential gene. The method is repeated further as needed to provide an HSV strain having all the desired nonessential gene deletions.

A second method comprises cotransfection of the ICP4ICP27 complementing cell line with the ICP4⁻ICP27⁻ HSV strain and pieces of DNA encoding for an inactivating mutation of the desired nonessential HSV gene. The pieces of DNA encoding for the inactivating mutation of the desired nonessential HSV gene may be contained within, for example, a plasmid, vector, HSV strain or other delivery vehicle. At some frequency homologous recombination will generate a ICP4⁻ICP27⁻ nonessential gene⁻ recombinant virus. The progeny of this cotransfection is then plated on ICP4ICP27 complementing cells and ICP4⁻ICP27⁻ nonessential gene(s)⁻ HSV strains are selected. Since there is no genetic selection for the ICP4⁻ICP27⁻ nonessential gene⁻ virus, Southern blot analysis of individual progeny isolates may be utilized to select ICP4⁻ICP27⁻ nonessential gene(s)⁻ HSV strain. The method may be performed again to produce further nonessential gene inactivations using the new ICP4⁻ICP27⁻ nonessential gene⁻ HSV strain and pieces of DNA encoding an inactivating mutation of a further nonessential HSV gene. The method is repeated further as needed to provide an HSV strain having all the desired gene inactivations.

It will be appreciated that the methods of generating ICP4⁻ICP27⁻ nonessential HSV gene(s)⁻ HSV strains disclosed hereinabove may be used together.

These methods are unique in that a novel ICP4ICP27 complementing cell line is used. By use of the novel cell line the ICP4⁻ICP27⁻ nonessential gene⁻ HSV strain can be generated, regardless of how much the growth of the novel strain is dampened due to incorporation of deletions or inactivating mutations in nonessential viral genes.

It will be appreciated that the present invention encompasses any method to generate ICP4⁻ICP27⁻ nonessential gene(s)⁻ HSV strains which use an ICP4ICP27 complementing cell line.

A specific example of a method utilizing the ICP4ICP27 complementing cell line, is the construction of a ICP4⁻ICP27⁻ICP0⁻ HSV strain. The gene for activator protein, ICP0, is located in the repeat sequences in the long component of the genome (See FIG. 1), and therefore, is present in two copies per genome. It is a promiscuous transactivator of test genes in transient assays, but the level at which it functions is still unclear. Given its potential role in gene expression as indicated from the transient assays, deletion of the ICP0 gene from the d92 background should reduce the cytotoxicity of d92. Genetic studies have shown that it is possible to delete both copies of the gene and obtain a virus that is viable in tissue culture but is extremely impaired for reactivation from explanted, latent trigeminal ganglia. While they remain viable, viruses deficient for ICP0 are impaired for growth in culture. The degree of impairment is minimized if the viruses are plaqued or propogated on cells seeded 8 hours earlier, presumably because of the availability of cellular factors present at that time in the cell cycle that lessen the requirement of ICP0.

The following procedure will inactivate the ICP0 gene in the d92 genome. The plasmid pW3-HS8 contains a 4.5 kb Sac I to Pst I insert which encodes the ICP0 gene. The initiator methionine codon for ICP0 is present in a unique Nco I site (CCATGG) in pW3-HS8. 700 bp into the protein coding sequence from NcoI is a unique Bam HI site. The sequence contained in the 700 bp NcoI-BamHI fragment will be replaced with the Bam HI fragment from the plasmid pSC8 (REF) that encodes the *E. coli* β-galactosidase gene. This will be done after deleting the 700 bp Nco I-Bam HI fragment and modifying the Nco I site in the ICP0 plasmid with synthetic linkers such that it will accept the β-gal-encoding Bam HI fragment and put the ATG in frame with the β-gal protein. This construction will put β-gal under ICP0 control. The resulting plasmid will be cleaved with Pst I, which cuts at the 3' boundary of the gene and the plasmid sequences, and cotransfected with d92 DNA onto 26 cells to generate the triple mutant virus. Recombinant virus plaques will be identified by staining with X-gal. Blue plaques will be picked and analyzed by Southern blot for the β-gal insertion genotype. Because ICP0 is a diploid gene, it is possible to obtain heterozygous viruses containing one intact ICP0 gene. Heterozygous viruses can be further plaque purified and analyzed by Southern blot to obtain homozygous mutant viruses. This approach has been used previously to generate mutant viruses in the ICP0 and other viral diploid and haploid genomes. Given that we can obtain stock titers of d92 in excess of $2 \times 10^9$, we should obtain stock titers of d92:ICP0⁻ in excess of $10^8$ on freshly seeded 26 cells. This represents the worst case scenario for the nonessential gene that has the greatest effect on vital yield (ICP0).

Although the plasmid pW3-HS8 is used in the procedure described hereinabove, it will be appreciated that the present invention encompasses the use of any vector which encodes an HSV nonessential gene and will transfect the novel ICP4⁺ICP27⁺ cell lines utilized.

Although the procedure described hereinabove utilizes a Bam HI fragment from the plasmid pSC8 that encodes the *E. coli* β-galactosidase gene so as to identify recombinant ICP0⁻ progeny, it will be appreciated that the present invention encompasses use of any fragment or any other method which allows identification of recombinant ICP4⁻ ICP27⁻ additional HSV gene(s)⁻ progeny.

It will be appreciated that, although the procedure described hereinabove produces novel recombinant ICP4⁻ICP27⁻ICP0⁻ HSV strains, the present invention encompasses any ICP4⁻ICP27⁻ One or more additional HSV genes⁻ HSV strains. Multiple additional HSV genes will be deleted or inactivated one gene at a time. It will be further appreciated that the present invention provides for novel HSV strains that are transcriptionally silent.

Many of the genes within the HSV genome are nonessential to virus reproduction. The present invention provides for novel ICP4⁻ICP27⁻ nonessential HSV gene(s)⁻ HSV strains. The present invention provides for methods of efficiently growing novel HSV strains deficient for ICP4, ICP27, and one or more nonessential HSV genes using the novel ICP4⁺ICP27⁺ cell lines disclosed herein. The method is the same as that used to efficiently grow d92 and comprises infecting 26 cells with the novel ICP4⁻ICP27⁻ nonessential HSV gene(s)⁻ HSV strains, incubating the infected cells, and collecting the progeny virus. It will be appreciated that this method may be used to grow ICP4⁻ICP27⁻ additional IE gene(s)⁻ HSV strains. The herpes virus needs no other IE gene coding proteins besides ICP4 and ICP27 to reproduce. Therefore, the 26 cell line will grow the additionally IE-gene-depleted virus.

As stated hereinbefore, the herpes virus has many properties which would be potentially useful for gene transfer purposes. The present invention provides for novel vectors comprising a novel HSV strain disclosed herein and at least one exogenous gene to be transferred to a cell and appropriate promoter sequences, wherein the gene to be transferred to a cell and the corresponding promoter sequence are contained within one or more nonessential regions of the genome of the novel HSV strains. The nonessential regions of the HSV genome are well known to those skilled in the art. The present invention also provides a method of using ICP4⁻ICP27⁻ HSV strains as vectors, wherein the method comprises inserting at least one exogenous gene and appropriate promoter sequence into the genomes of the ICP4⁻ICP27⁻ HSV strain, and then infecting cells with the ICP4⁻ICP27⁻ HSV strain. The present invention also provides a method of using ICP4⁻ICP27⁻ additional HSV gene(s)⁻ HSV strains as vectors, wherein the method comprises inserting at least one exogenous gene and appropriate promoter sequence into the genomes of the ICP4⁻ICP27⁻ additional HSV gene(s)⁻ HSV strain, and then infecting a cell with the ICP4⁻ICP27⁻ HSV gene(s)⁻ HSV strain.

The inventor has demonstrated that $10^4$ to $10^5$ functional d92 viral genomes persisting in $10^6$ HEL cells at one to two weeks post-infection. This gives a lower limit on the amount of vector delivered DNA persisting in the cells at these times. This efficiency is bound to increase with further HSV gene deletions, which reduce the cytotoxicity of d92. Given the occurrence of a substantial number of persisting genomes, it follows that integration events through nonhomologous recombination will occur between the persisting viral genome and the cellular DNA. Several observations support the occurrence of extremely efficient gene transfer: (1) DNA introduced into mammalian cells is often integrated in nonhomologous sites; (2) Ultraviolet (UV) inactivated HSV were the first virus vehicles used to transform tk⁻ cells to the tk⁺ phenotype. UV irradiated virus were able to transform cells at low frequencies. For this purpose, high doses of UV are required to inactivate virus stocks to the level that residual infectivity is not a problem. Under these circumstances, the transforming DNA is certain to have incurred significant UV damage; an undesirable property when one wishes to introduce biologically active genetic information. The use of nonirradiated, noncytotoxic vectors would obviate this problem; and (3) This has recently been accomplished for an ICP4⁻ virus transforming cells with the neomycin resistance gene.

While the ICP4⁻ viruses have been shown capable of introducing transforming DNA into cultured cells, several observations suggest that d92 and additional HSV gene deficient viruses will be more efficient: (a) The level of recombinants in the ICP4⁻ICP27⁻ system are far lower than the lowest obtainable in the ICP4⁻ system. This will allow us to routinely use higher moi's without the fear of the presence of chance wild-type recombinants; (b) More persistent genomes are obtainable with d92 than ICP4⁻ viruses (preliminary results); and (c) Further mutational alterations made on d92 that reduce its cytotoxicity will also increase its transformation efficiency.

The present invention provides that vectors may be produced from the novel HSV strains disclosed herein by any known techniques, including, but not limited to, classical genetic or recombinant techniques. In addition, the novel vectors may be utilized by known methods. For example, a vector for neomycin resistance may be produced and utilized. The gene encoding the bacterial protein neomycin phosphotransferase is contained on the plasmid pSV2neo under the control of the SV40 promoter. The entire gene with the promoter will be placed in the Sac 1 site within the cloned HSV tk gene. The resulting plasmid will be cotransfected with recipient intact viral DNA on complementing 26 cells. The progeny of the transfection will be plated on 26 cells in the presence of acycloguanosine (1×10⁻4M) for the selection of the tk⁻ phenotype. Southern blots on small cultures from individual plaque isolates will be performed to identify the introduced neoʳ gene. The desired viruses will be further plaque purified and stocks will be prepared on 26 cells. Veto cells will be used as recipients for the neoʳ virus. The stable presence and function of the gene in transformed cells will be selected for by incubation in the drug G418.

As another example, a vector for the human HPRT gene may be produced and utilized. The human HPRT gene under the control of the HSV tk promoter has been cloned into the tk gene of wild-type HSV. This virus is referred to as HSV-HP40. HSV-HP40 and d92 (or its derivatives) will be coinfected on 26 cells in a classical cross equipment. Progeny that grow in the presence of acycloguanosine (tk interrupted by HPRT) on 26 cells, but not on Vero cells (containing the mutations in ICP4 and ICP27) will be isolated and the genomes examined by Southern blot hybridization to confirm the presence of all the alleles. The distance between ICP27 and tk is great enough to allow 20%–30% recombination. B103-4C cells are a HPRT derivative of B103 rat neuroma cells. Infected B103-4 be incubated in HAT medium to select for HPRT⁺ transformants. HAT medium contains 110 mM hypozanthine, 2.3 mM aminoptrin, and 20 mM thymidine. The same mechanical procedures will be used for the cloning and DNA analysis of B103-4C cells as were used for Vero cells above.

It will be appreciated that the present invention encompasses use of the novel HSV strains disclosed herein as vectors carrying any genes whose size permits them to be inserted in the HSV genome. It will be further appreciated that the novel vectors disclosed herein may be utilized for gene therapy and other known vector uses.

The unique properties of the herpes virus allow the novel HSV strains disclosed in the present invention to be used for mutational inactivation of normal cellular genes or for the repair of mutant cellular genes, by homologous recombination. The present invention provides for a method of directing homologous, site-specific recombination in cellular DNA, wherein the method comprises infecting a cell with a large quantity of a vector, wherein the vector comprises: (1) an HSV strain whose genome is deficient for the HSV genes encoding the proteins ICP4 and ICP27 or the proteins ICP4, ICP27, and one or more additional HSV genes, and (2) a gene to be transferred contained with one or more nonessential regions of the HSV genome, the gene to be transferred being homologous to a gene existing within the cell.

The creation of sequence specific alterations in DNA has long been the goal of genetic research. It allows for the precise elimination and repair of biological function. In simple systems, this often involves the routine practice of generating genetic recombinants through the cross over of DNA sequences that share sequence identity. From the standpoint of altering the genome of the mammalian cell in a defined way, the generation of site-specific recombinants has been possible but occurs at a very low frequency. It has long been known that DNA introduced into mammalian cells is integrated into nonhomologous sites. Given that homologous recombination between specific sequences in the chromosome and introduced DNA occurs at a very low frequency, it follows that a nontoxic method to introduce numerous copies of homologous DNA into all the cells in a given culture would be desirable for this purpose. In addition, if the homologous DNA is vectored into the target cells by a genome that has evolved a mechanism to persist in those cells, this adds to the probability that homologous events will occur. The novel herpes virus vectors of the present invention uniquely meet these criteria. In addition, the large capacity of HSV for exogenous DNA is desirable from the standpoint of transducing genomic copies of cellular genes.

An example of a method of directing site-specific homologous recombination would be the homologous knock-out of the HPRT gene. The SV40 neogene will be inserted into a 10.5 kb piece of human DNA that encodes exons 4 and 5 of human HPRT, such that exon 4 is deleted. This piece of DNA is contained on an Eco R1 fragment. This entire cassette will be inserted at the 3' end of the HSV tk gene. The tk gene contains a mutation that confers temperature sensitivity and is under the control of the stronger ICP4 promoter instead of the tk promoter. The HSV sequences that flank the tk gene in the proposed genome flank the construct. The constructed plasmid will be cotransfected with the appropriate intact HSV vector DNA onto 26 cells. The progeny of the transfection will be plated at 39.6° C. in the presence of acycloguanosine (100 μM) for the selection of tk⁻ virus. Homologous recombination, introducing the ts tk into the genome will result in a tk⁻ phenotype at the elevated temperature. Plaques isolated at 39.6° C. will be amplified and analyzed by Southern blot for the presence of the HPRT and neo DNA linked to the ts tk gene.

The HPRT:neo transducing virus will be used to infect human HepG2 cells. HepG2 cells are a hepatocellular carcinoma cell line derived from a human male. G418 will select for stable integration events, as above. These events can be either nonspecific or homologous. Gancyclovir ($2 \times 10^{-6}$ M) selection will be simultaneously applied to such against the integration of tk along with the neo gene. This procedure has been previously shown to enrich for homologous recombination events which naturally should exclude the tk gene. In addition, 6-thioguanine (14 µg/ml) selection will also be applied to select for inactivation of the HPRT protein by the interruption of part of the gene. Isolated colonies will be analysed by Southern blots to ascertain that the homologous event occurred. The above scheme uses the tk gene within the HSV genome, the large capacity for foreign DNA in the HSV genome, and three strong selections to site-specifically inactivate the HPRT gene.

The larger the DNA sequence being transferred, and the greater the amount of virus infecting the cell, the greater the amount of homologous recombination. It will be appreciated that the present invention encompasses using the novel HSV strains disclosed herein to produce homologous recombinations with any DNA segment which has a homologous cellular DNA counterpart and which may be carried by the herpes virus.

EXAMPLE 1

Construction Of 26 Cells

The plasmid PSV2 neo contains the gene encoding neomycin phosphoryl transferase and confers resistance to G418 to mammalian cells. The plasmid pK1-2 contains the coding sequence and transcriptional regulatory elements for the expression of ICP4. (See DeLuca, N. A. et al., *Nucleic Acids Res.*, 15:4491–4511, 1987.) It contains approximately 400 bp of HSV-1 sequences beyond the 3' end of the mRNA. The plasmid pKHX-BH contains all the coding sequence of HSV necessary to express ICP27. (See Bond, V. C. et al, *Virology*, 132:368–376, 1984.) pSV2neo (1 microgram), pK1-2 (3 micrograms), and pKHX-BH (3 micrograms) were cotransfected using the calcium phosphate precipitation method onto $4 \times 10^6$ ATCC CCL81 Vero cells. Four hours after the application of the precipitate to the cells, they were subjected to a 15% glycerol shock for a period of 2 mins. After the shock, the cells were incubated in DME plus 10% FBS at 37° C. 24 hours later, the cells were trypsinized and replated at one tenth the original density and G418 was applied (1 mg/ml). After four days, the concentration of G418 was lowered to 400 micrograms per ml. After two weeks, G418 resistant colonies were observed. These were isolated and expanded. Monolayer cultures from individual clones were infected with d120, to determine the functional presence of the ICP4 gene, and 5dl 1.2, to determine the functional presence of the ICP27 gene.

Of the 67 cell lines tested with d120 and 5dl 1.2, 12 allowed the growth of only d120, 4 allowed the growth of only 5dl 1.2 and, 19 of the lines allowed the growth of both. With many of the lines that allowed the growth of both, virus yield experiments were performed to determine the best cell line to use as an efficient host for both mutant viruses. The plaque of d120 and 5dl 1.2 were closest in size to wild-type virus on a cell line designated 26 cells. The yields of d120 and 5dl 1.2 were 810 and 310 PFU/cell, respectively on 26 cells. A cell line designated 8 cells were also retained because they only allowed the efficient growth of 5dl 1.2.

EXAMPLE 2

Construction Of d92, An ICP4 and ICP27 Deletion Mutant d120 and 5dl 1.2 were used to coinfect 26 cells at an moi of 5 PFU each. 18 hours later the culture was harvested and the progeny were plated out on 26 cells for the isolation of individual plaques. After the plaques developed, they were picked with a pipet into 0.5 ml medium, freeze-thawed three times and plated on 26 cells (ICP4 and ICP27 complementing), E5 cells (ICP4 complementing), 8 cells (ICP27 complementing), and Veto cells (noncomplementing). 120 plaque isolates were tested. 29 (24%) of the progeny grew only on E5 cells and 26 cells; these are the ICP4 mutant parent. 63 (53%) grew only on 8 cells and 26 cells; these are the ICP27 mutant parent. 18 (15%) grew on all the cell types; these are wild-type virus recombinants generated by the cross over of DNA from d120 and 5dl 1.2. 10 (8.3%) only grew on 26 cells; these are the ICP27$^-$ICP4$^-$ double mutant. These were checked by Southern blot analysis for the presence of the deletion characteristic of both d120 and 5dl 1.2.

It will be appreciated that the present invention discloses novel ICP4$^+$ICP27$^+$ cell lines; a method of producing ICP4$^+$ ICP27$^+$ cell lines; novel ICP4$^-$ICP27$^-$ HSV strains, their generation, and use as vectors; ICP4$^-$ICP27$^-$ additional HSV gene(s)$^-$ HSV strains, their generation, and use as vectors; novel vectors comprising the novel HSV strains disclosed herein whose genome contains at least one exogenous gene and an appropriate promoter sequence; methods of using the novel HSV strains disclosed herein as vectors; and methods of using the novel HSV disclosed herein to direct homologous recombination with cellular DNA.

The following cell line and HSV-1 mutant viral strain were deposited with the American Type Culture Collection (ATCC), 12301 Parklawn Drive, Rockville, Md. 20852 on Apr. 21, 1993, and assigned accession numbers as follows:

|  | Accession No. |
| --- | --- |
| Cell line "26 cells" | CRL 11332 |
| HSV-1 strain "d92" | VR 2406 |

Whereas particular embodiments of the invention has been described hereinbefore, for purposes of illustration, it would be evident to those skilled in the art that numerous variations of the details may be made without departing from the invention as defined in the appended claims.

What is claimed:

1. A cell line containing DNA encoding both the HSV proteins ICP4 and ICP27.

2. The cell line of claim 1, wherein said DNA encoding ICP4 is contained within a plasmid and wherein said DNA encoding ICP27 is contained within a plasmid.

3. The cell line of claim 1, wherein said cells are Vero cell derivatives.

4. The cell line of claim 2, wherein said plasmid encoding ICP4 is pK1-2 and wherein said plasmid encoding ICP27 is pKHX-BH.

5. The cell line of claim 4 which is 26 cells, deposited with the ATCC and assigned accession number CRL 11332.

6. A method of producing a cell line containing DNA encoding the HSV proteins ICP4 and ICP27, said method comprising: cotransfecting cells capable of hosting HSV with pieces of DNA encoding the HSV protein ICP4 and pieces of DNA encoding the HSV protein ICP27; incubating said cells; and selecting cells harboring both ICP4 and ICP27 encoding pieces of DNA.

7. The method of claim 6, including cotransfecting said ICP4 encoding pieces of DNA and said ICP27 encoding pieces of DNA into said cells with pieces of DNA encoding a selection factor; and selecting cells expressing said selection factor.

8. The method of claim 6, wherein
said cells capable of hosting HSV are Vero cells.

9. The method of claim 6, wherein said pieces of DNA encoding ICP4 and pieces of DNA encoding ICP27 are contained within plasmids.

10. The method of claim 7, wherein said pieces of DNA encoding a selection factor are pSV2neo plasmids, and cells harboring said pSV2neo are selected by isolating cells resistant to G418.

11. The method of claim 7, wherein said pieces of DNA encoding ICP4, said pieces of DNA encoding ICP27, and said pieces of DNA encoding a selection factor are cotransfected onto said cells capable of hosting HSV by the calcium phosphate precipitation method.

12. The method of claim 9, wherein said plasmid containing ICP4 is pK1-2 and said plasmid containing ICP27 is pKHX-BH.

13. An HSV strain whose genome is deficient for the HSV genes encoding ICP4 and ICP27.

14. The HSV strain of claim 13, wherein
said genome is further deficient for at least one additional HSV gene.

15. The HSV strain of claim 13 which is d92, deposited with the ATCC and assigned accession number VR 2406.

16. The HSV strain of claim 14, wherein said additional HSV gene is a nonessential HSV gene.

17. The HSV strain of claim 14, wherein said additional HSV gene is the HSV gene encoding ICP22.

18. The HSV strain of claim 14 wherein said additional HSV gene is the HSV gene encoding ICP6.

19. The HSV strain of claim 14 wherein said additional HSV gene is the HSV gene encoding ICP47.

20. A method of producing an HSV strain whose genome is deficient for the HSV genes encoding ICP4 and ICP27, said method comprising: coinfecting ICP4ICP27 complementing cells containing DNA encoding the HSV proteins ICP4 and ICP27 with an HSV strain deficient for the ICP4 gene and an HSV strain deficient for the ICP27 gene; incubating said cells; plating virus progeny from said incubated cells on ICP4ICP27 complementing cells, ICP27 complementing cells, ICP4 complementing cells, and ICP4⁻ICP27⁻ cells; picking plaques; and identifying virus that plaque on ICP4ICP27 complementing cells and do not plaque on ICP27 complementing cells, ICP4 complementing cells, or ICP4⁻ICP27⁻ cells.

21. The method of claim 20, wherein said HSV strain deficient for the ICP4 gene is dl20 and said HSV strain deficient for the ICP27 gene is 5dl 1.2.

22. The method of claim 20, wherein
said ICP4⁻ICP27⁻ cells are Vero cells.

23. The method of claim 20, wherein
said ICP4 complementing cells are E5 cells.

24. A method of growing an HSV strain whose genome is deficient for the HSV genes encoding ICP4 and ICP27, said method comprising: infecting ICP4 ICP27 complementing cells containing DNA encoding the HSV proteins ICP4 and ICP27 with said HSV strain whose genome is deficient for the HSV genes encoding ICP4 and ICP27; incubating said infected ICP4 ICP27 complementing cells; and collecting virus progeny produced by said incubated cells.

25. The method of claim 24, wherein said genome of said HSV strain is further deficient for at least one additional HSV gene.

26. The method of claim 25, wherein said additional HSV gene is a nonessential HSV gene.

27. The method of claim 25, wherein said additional HSV gene is the HSV gene encoding ICP22.

28. The method of claim 25, wherein said additional HSV gene is the HSV gene encoding ICP6.

29. The method of claim 25, wherein said additional HSV gene is the HSV gene encoding ICP47.

30. A vector comprising: an HSV strain whose genome is deficient for the HSV genes encoding the proteins ICP4 and ICP27, at least one exogenous gene to be transferred to a cell, and an appropriate promoter sequence, wherein said exogenous gene and said promoter sequence are contained within one or more nonessential regions of said HSV genome.

31. The vector of claim 30, wherein said genome is further deficient for at least one additional HSV gene.

32. The vector of claim 31, wherein said additional HSV gene is a nonessential HSV gene.

33. The vector of claim 31, wherein said additional HSV gene is the HSV gene encoding ICP22.

34. The vector of claim 31, wherein said additional HSV gene is the HSV gene encoding ICP6.

35. The vector of claim 31, wherein said additional HSV gene is the HSV gene encoding ICP47.

36. A method of using an ICP4⁻ICP27⁻ HSV strain as a vector, said method comprising: inserting at least one exogenous gene and an appropriate promoter sequence into said ICP4⁻ICP27⁻ HSV strain's genome; and then infecting cells with said ICP4⁻ICP27⁻ HSV strain.

37. The method of claim 36, wherein said ICP4⁻ICP27⁻ HSV strain is further deficient for at least one additional HSV gene.

38. The method of claim 37, wherein said additional HSV gene is a nonessential HSV gene.

39. The method of claim 37, wherein said additional HSV gene is the HSV gene encoding ICP22.

40. The method of claim 37, wherein said additional HSV gene is the HSV gene encoding ICP6.

41. The method of claim 37, wherein said additional HSV gene is the HSV gene encoding ICP7.

42. A method of producing an HSV strain whose genome is deficient for the HSV genes encoding ICP4 and ICP27, and at least one additional HSV gene, said method comprising: coinfecting ICP4ICP27 complementing cells containing DNA encoding the HSV proteins ICP4 and ICP27 with an ICP4⁻ICP27⁻ HSV strain and an HSV strain deficient for at least one additional HSV gene; incubating said cells; plating virus progeny from said incubated cells on said ICP4ICP27 complementing cells; and selecting a resultant ICP4⁻ICP27⁻ HSV strain whose genome is further deficient for at least one additional HSV gene.

43. The method of claim 42, including selecting said resultant ICP4⁻ICP27⁻ HSV strain whose genome is further deficient for at least one additional HSV gene by Southern blot analysis.

44. The method of claim 42, wherein said additional HSV gene is a nonessential HSV gene.

45. The method of claim 42, wherein said additional HSV gene is the HSV gene encoding ICP22.

46. The method of claim 42, wherein said additional HSV gene is the HSV gene encoding ICP6.

47. The method of claim 42, wherein said additional HSV gene is the HSV gene encoding ICP47.

48. A method of producing an HSV strain whose genome is deficient for the HSV genes encoding ICP4 and ICP27, and at least one additional HSV gene, said method comprising: cotransfecting ICP4ICP27 complementing cells containing DNA encoding the HSV proteins ICP4 and ICP27 with an ICP4⁻ICP27⁻ HSV strain and pieces of DNA encoding an inactivating mutation of at least one additional HSV gene; incubating said cells; plating virus progeny from said incubated cells on ICP4ICP27 complementing cells; and selecting a resultant $ICP4^-ICP27^-$ HSV strain whose genome is further deficient for at least one additional HSV gene.

49. The method of claim 48, including selecting said resultant $ICP4^-ICP27^-$ HSV strain whose genome is further deficient for at least one additional HSV gene by Southern blot analysis.

50. The method of claim 48, wherein said pieces of DNA encoding an inactivating mutation of at least one additional HSV gene are contained within plasmids.

51. The method of claim 48, wherein said additional HSV gene is a nonessential HSV gene.

52. The method of claim 48, wherein said additional HSV gene is the HSV gene encoding ICP22.

53. The method of claim 48, wherein said additional HSV gene is the HSV gene encoding ICP6.

54. The method of claim 48, wherein said additional HSV gene is the HSV gene encoding ICP47.

55. A method of generating a HSV mutant virus dependent upon complementing functions of ICP4 and ICP27 for growth, which comprises: infecting an $ICP4^{(+)}/ICP27^{(+)}$ cell line expressing complementing levels of ICP4 and ICP27 with said HSV mutant virus; incubating said cell line in the appropriate medium; and, collecting said HSV mutant virus produced by said cell line.

56. The method of claim 55 wherein said mutated HSV virus is deficient for the genes encoding ICP4 and ICP27.

57. The method of claim 55 wherein said cell line is 26 cells, deposited with the ATCC and assigned accession number CRL 11332.

58. The method of claim 56 wherein said mutated virus is d92, deposited with the ATCC and assigned accession number VR 2406.

59. The method of claim 56 wherein said cell line is 26 cells, deposited with the ATCC and assigned accession number CRL 11332.

60. The method of claim 58 wherein said cell line is 26 cells, deposited with the ATCC and assigned accession number CRL 11332.

* * * * *

UNITED STATES PATENT AND TRADEMARK OFFICE
CERTIFICATE OF CORRECTION

PATENT NO. : 5,658,724
DATED : August 19, 1997
INVENTOR(S) : Neal A. DeLuca

It is certified that error appears in the above-identified patent and that said Letters Patent is hereby corrected as shown below:

ON THE TITLE PAGE:

[56] References Cited; Other Publications: Column 2, line 3: "ICP24" should read --ICP4--.

[56] References Cited; Other Publications: Column 2, line 5: "ICP24" should read --ICP4--.

IN THE DRAWINGS:

Sheets 2 of 4 through 4 of 4 should be deleted and substitute the attached sheets 2 of 4 through 4 of 4 therefore.

In Column 2, line 6: "198." should read --1987--.

In Column 8, line 39: "There" should read --These--.

In Column 13, line 36: "genewith" should read --gene with--.

In Column 13, line 41: "(1x10-4M)" should read --($1 \times 10^{-4}M$)--.

In Column 13, line 46: "Veto" should read --Vero--.

In Column 14, line 47: "neogene" should read --neo gene--.

In Column 16, line 6: "Veto" should read --Vero--.

IN THE CLAIMS:

In Column 18, line 37: "ICP7" should read --ICP47--.

Signed and Sealed this

Seventeenth Day of March, 1998

*Attest:*

BRUCE LEHMAN

*Attesting Officer*  *Commissioner of Patents and Trademarks*